United States Patent [19]

Himmele et al.

[11] Patent Number: 4,929,786
[45] Date of Patent: May 29, 1990

[54] PREPARATION OF 1-ARYL-1-ALKENES

[75] Inventors: Walter Himmele, Walldorf; Kaspar Bott, Mannheim; Klaus Bronstert, Carlsberg, all of Fed. Rep. of Germany

[73] Assignee: BASF Aktiengesellschaft, Ludwigshafen, Fed. Rep. of Germany

[21] Appl. No.: 264,081

[22] Filed: Oct. 28, 1988

[30] Foreign Application Priority Data

Oct. 30, 1987 [DE] Fed. Rep. of Germany ....... 3736819

[51] Int. Cl.$^5$ ................................................ C07C 1/20
[52] U.S. Cl. ..................................... 585/469; 568/640; 570/128; 585/435
[58] Field of Search ................ 585/469, 435; 568/640; 570/128

[56] References Cited

U.S. PATENT DOCUMENTS 4,049,573  9/1977  Kaeding .............................. 585/469
4,207,424  6/1980  Winnick .............................. 585/469

FOREIGN PATENT DOCUMENTS 2401126  3/1979  France .
61-072727  4/1986  Japan .................................. 585/469

OTHER PUBLICATIONS

Houbin-Weyl, Method in Organic Chemistry, vol. V/1b, pp. 45–62, pp. 70–104, (1972).

Primary Examiner—H. M. S. Sneed
Assistant Examiner—J. Saba
Attorney, Agent, or Firm—Keil & Weinkauf

[57] ABSTRACT

Preparation of 1-aryl-1-alkenes by dehydration of 1-aryl-1-alkanols in the presence of a substance promoting elimination of water, the substance being a triester of phosphorous acid in which at least one of the radicals is an aryl group.

The products are suitable as, inter al., initiators for anionic polymerization.

5 Claims, No Drawings

PREPARATION OF 1-ARYL-1-ALKENES

The present invention relates to a process for the preparation of 1-aryl-1-alkenes by dehydration of 1-aryl-1-alkanols in the presence of a substance promoting elimination of water.

A number of methods for the preparation of 1-aryl-1-alkenes from the corresponding 1-aryl-1-alkanols have been described. A comprehensive compilation of the dehydration methods is found in Houben-Weyl, *Methoden der organischen Chemie*, 4th ed., vol. 5/1b, pp. 45–62 & 70–104, Georg Thieme Verlag, Stuttgart (1972). According to information given therein dehydration can be carried out in both the liquid and the gaseous phase. In the liquid phase both acid and basic compounds are said to catalyze the elimination of water. Recommended acid catalysts include sulfuric, p-toluenesulfonic, phosphoric, boric, and formic acids, acetic and phthalic anhydrides, and compounds such as potassium hydrogen sulfate and copper sulfate.

These acid compounds do in fact catalyze the elimination of water from 1-aryl-1alkanols very well on the whole, but they have distinct disadvantages. When strong acids are used, considerable proportions of side products are formed because the olefins formed enter into further reactions, such as polymerization or alkylation of aromatic rings.

There is also the possibility of proton-catalyzed isomerization involving the double bond and of migration of alkyl groups under the strongly acid reaction conditions used hitherto. If the products carry groups that are labile in the presence of acids (such as ether groups) these can lead to further side reactions.

The use of these catalysts also makes it practically impossible to isolate the product by direct distillation of the reaction mixture. Instead it is necessary to work up the mixture continuously in several stages, viz. neutralization, extraction, and then distillation.

Furthermore, employment of some of the catalysts mentioned leads to the formation of deposits and incrustations on the walls of the reaction vessel, which then have to be subjected to a laborious cleaning treatment to remove the deposits and incrustations.

Several of the catalysts used previously would bind the water formed in the reaction, making it impossible to remove it from the reaction mixture by distillation. Since however the amount of water formed is a measure of the degree of conversion, it would be desirable to be able to distill off the water of reaction continuously.

The aim of the present invention was therefore to provide a process for the dehydration of 1-aryl-1-alkanols to 1-aryl-1-alkenes that, without suffering from the disadvantages of previous methods, makes it possible to isolate the product from the reaction mixture by direct distillation, without previous treatment, and also allows the water of reaction to be distilled off from the reaction mixture continually.

In accordance with this aim we have found a process for the preparation of 1-aryl-1-alkenes by dehydration of 1-aryl-1-alkanols in the presence of a substance promoting elimination of water which is a triester of phosphorous acid having at least one aryl group.

The novel process can be described by the general equation

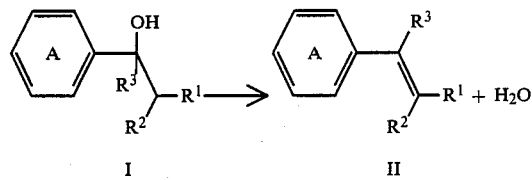

where not more than two of the radicals $R^1$, $R^2$, and $R^3$ are hydrogen and the remainder are radicals that are inert under the conditions of the reaction. Inert radicals are, for instance, aryls and alkyls. The latter can however be substituted by cycloalkyls, aryls, or alkoxy radicals. The ring A and any other aryls may be substituted by, for instance, alkyl, alkoxy, fluoro, chloro, or bromo radicals or fused rings.

The radicals $R^1$, $R^2$, and $R^3$ are preferably hydrogen or branched or unbranched alkyls of from 1 to 18 carbon atoms, for example; the alkyls can be substituted by phenyl. The preferred substituents for the ring A include fluorine and chlorine. Examples of preferred alkyls are methyl, ethyl, propyl, isopropyl, hexyl, isohexyl, 2-ethylhexyl, octyl, decyl, dodecyl, and hexadecyl.

The aryl phosphites used in the novel process are triesters of phosphorous acid of the general formula (III)

$$R^4O\text{—}P(OR^5)\text{—}OR^6 \qquad (III)$$

where the radicals $R^4$, $R^5$, and $R^6$ are identical or different and can be aryls, alkyls of from 1 to 20 carbon atoms, arylalkyls of from 7 to 20 carbon atoms, or cycloalkyls of from 3 to 8 carbon atoms, provided that at least one of these radicals is an aryl.

Diaryl and triaryl phosphites such as alkyl diphenyl phosphites and triphenyl phosphites, or the corresponding compounds in which the phenyl radicals are substituted by alkyl, are especially suitable for promoting the elimination of water. Examples are hexyl diphenyl or cyclohexyl diphenyl phosphite and (these are preferred) triphenyl or tritolyl phosphites.

Preferably catalytic proportions of the phosphites are used. For instance, the mass fraction of phosphite ester in the mixture can be from 0.05% to 2%, especially from 0.2% to 1%.

In general suitable temperatures for dehydration lie in the range of from 120° C. to 225° C., preferably between 140° C. and 200° C. As a rule conversions of more than 90% are attained with reaction times of a few hours.

It has proved especially advantageous to remove the water of reaction by distillation with an entrainer that is immiscible with and less dense than water. The volume of the lower (aqueous) phase that separates from the condensate can then be used as a measure of conversion. Once the required conversion is reached the reaction can be broken off in order to avoid unnecessary exposure of the olefin to heat. Suitable entrainers for water include alkanes with a medium number of carbon atoms and alkyl-substituted benzenes such as toluene, xylenes, and diisopropylbenzenes.

After dehydration has been carried out, it is expedient to separate the products by fractional distillation of the reaction mixture. Distillation can be carried out without previous treatment of the mixture. Further details of the novel process are described in the Examples.

The 1-aryl-1alkanols required for preparation of 1-aryl-1-alkenes by the novel process can be synthesized from the appropriate Grignard reagents and aldehydes or ketones (cf. Tables 1–5), as described in Organikum, pp. 618ff., Deutscher Verlag der Wissenschaften, Berlin (1976), or by the Guerbet reaction from appropriate alcohols (cf. Table 6), as described in, for instance, EP-A 0 227 057.

The 1-aryl-1-alkenes that can be prepared by means of the novel process are valuable intermediates for initiators used in anionic polymerizations (cf. European Patent Application P 37 29 144.0, for example).

EXAMPLE 1

Preparation of 1-(p-chlorophenyl)-1-octene by the dehydration of 1-(p-chlorophenyl)-1-octanol In a 2-1 flask fitted with stirrer, water separator, dropping funnel, and thermometer was placed 1109 g (4.60 mol) of 1-(p-chlorophenyl)-1-octanol, and 10 g (0.9%) of triphenyl phosphite was added to catalyze the dehydration. A mixture of octane and xylenes was used to entrain the water of reaction. The temperature of the mixture was adjusted to 194–6° C.

In the course of 5 h, 67 g of water was withdrawn from the water separator. After addition of another 5 g of triphenyl phosphite (making 1.35% in all), a further 8 g of water was obtained in 5 h, during which time the temperature was maintained at 193–8° C. The total quantity of water obtained was 75 g (4.16 mol), corresponding to 90.6% of the theoretical amount.

The 1-(p-chlorophenyl)-1-octene was isolated and purified by fractional distillation of the untreated reaction mixture through a sieve-plate column with 10 plates. Under a pressure of 20 mbar, 919 g of 1-(p-chlorophenyl)-1-octene distilled over between 130° C. and 132° C. The first fractions contained small proportions of the Z-isomer, but 92% of the product was (E)-1-(p-chlorophenyl)-1-octene.

The total yield of 1-(p-chlorophenyl)-1-octene was 89.6%.

EXAMPLE 2

Preparation of 1-(p-fluorophenyl)-3,5,5-trimethyl-1-hexene by the dehydration of 1-(p-fluorophenyl)-3,5,5-trimethyl-1hexanol At a temperature of from 168° C. to 184° C., 350 g of 1-(p-fluorophenyl)-3,5,5-trimethyl-1-hexanol was dehydrated in the presence of 5 g of tri-o-tolyl phosphite and a 1:2-mixture of octane and xylenes over a period of 10 h. The mass of water obtained was 22 g, corresponding to 83.7% of the theoretical amount.

Fractional distillation of the untreated reaction mixture through a sieve-plate column with 10 plates gave 282 g (1.28 mol) of the required olefin, which under a pressure of 8 mbar distilled over between 110° C. and 114° C. The first fractions contained small proportions of the Z-isomer, but about 90% of the product was (E)-1-(p-fluorophenyl)-3,5,5-trimethyl-1-hexene.

The total yield of 1-(p-fluorophenyl)-3,5,5-trimethyl-1-hexene was 87.2%, based on the quantity of 1-(p-fluorophenyl)-3,5,5- trimethyl-1-hexanol, which had not been specially purified after its synthesis from the Grignard compound of 1-bromo-4-fluorobenzene and 3,5,5-trimethylhexanal.

FURTHER EXAMPLES (Tables 1–5, Compounds 1–48)

Table 1 lists 1-(4-fluorophenyl)-1-alkenes prepared in accordance with the novel process. The 1-(4-fluoro)-1-alkanols required, which are all known and mostly available commercially, were synthesized either from 4-fluorobenzaldehyde and the Grignard reagent of the appropriate halogen compound or from the Grignard reagent of 1-bromo-4-fluorobenzene and the appropriate aldehyde or ketone.

4-Methyl-4-phenylvaleraldehyde, required for the synthesis of Compound 6, was prepared from the appropriate alkene (cf. EP-A 0 219 092) by hydroformylation, as described in Houben-Weyl, *Methoden der organischen Chemie*, 4th ed., vol. 7/1, Georg Thieme Verlag, Stuttgart (1972). 3,5,5-Trimethylhexanal, required for the synthesis of Compound 10, was prepared similarly from isobutylene dimer (Houben-Weyl, ibid., p. 58).

Table 2 lists 1-(4-chlorophenyl)-1-alkenes and 1-92-chlorophenyl)-1-alkenes. The 1-aryl-1-alkanols required were prepared from 4-chlorobenzaldehyde or 2-chlorobenzaldehyde and the Grignard reagent of the appropriate halogen compound.

Tables 3–5 list various 1-aryl-1-alkenes obtained from 1-aryl-1-alkanols synthesized from the appropriate aldehydes or ketones and the Grignard reagents of bromobenzene, 1-bromo-4-methoxybenzene, and 1-bromo-4-fluorobenzene.

Table 6 lists 1-aryl-1-alkenes obtained from 1-aryl-1-alkanols prepared from known compounds by the Guerbet reaction.

The tables give the (non-optimized) yields of the products, based on the starting amounts of 1-aryl-1-alkanols, and the boiling ranges.

TABLE 1

Synthesis of 1-(4-fluorophenyl)-1-alkenes, starting from 4-fluorobenzaldehyde or 4-fluoro-1-bromobenzene

| Structural formula | Ser. | Yield/% | boiling range t/°C. | p/mbar |
|---|---|---|---|---|
| | 1 | 85 | 65–6 | 10 |
| | 2 | 82.0 | 126 | 2 |
| | 3 | — | m.p. 108—13) | |
| | 4 | 78 | 95 | 28 |
| | 5 | 61 | 80 | 23 |
| | 6 | 72 | 140 | 2 |

TABLE 1-continued

Synthesis of 1-(4-fluorophenyl)-1-alkenes, starting from 4-fluorobenzaldehyde or 4-fluoro-1-bromobenzene

| Structural formula | Ser. | Yield/% | boiling range t/°C. | p/mbar |
|---|---|---|---|---|
| 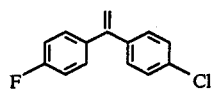 | 7 | — | 108 | 1 |
| 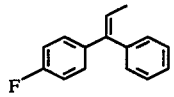 | 8 | 91 | 87 | 3 |
| 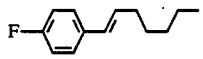 | 9 | 87.8 | 87 | 2 |
| 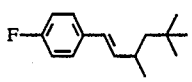 | 10 | 87.2 | 110-14 | 8 |

TABLE 2

Synthesis of 1-(chlorophenyl)-1-alkenes, starting from 4-chlorobenzaldehyde or 2-chlorobenzaldehyde

| Structural formula | Ser. | Yield % | boiling range t/°C. | p/mbar |
|---|---|---|---|---|
| 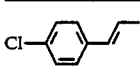 | 11 | 80.0 | 100 | 20 |
| 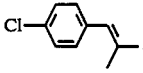 | 12 | 69.0 | 117 | 30 |
| 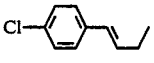 | 13 | 69.5 | 71-2 | 2 |
| 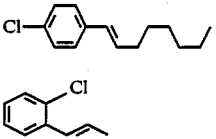 | 14 | 89.6 | 130-2 | 2 |
|  | 15 | 77.0 | 121-2 | 32 |
|  | 16 | 71.7 | 120 | 30 |
| 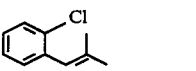 | 17 | 75.8 | 103 | 2 |
|  | 18 | — | 76-82 | 2 |

TABLE 3

Synthesis of 1-phenyl-1-alkenes, starting from bromobenzene and special rhodium oxo aldehydes

| Structural formula | Ser. | Yield/% | Boiling range t/°C. | p/mbar |
|---|---|---|---|---|
| 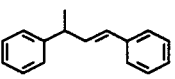 | 19 | 97.0 | 138-42 | 4 |

TABLE 3-continued

Synthesis of 1-phenyl-1-alkenes, starting from bromobenzene and special rhodium oxo aldehydes

| Structural formula | Ser. | Yield/% | Boiling range t/°C. | p/mbar |
|---|---|---|---|---|
| 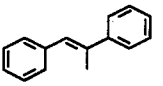 | 20 | 93.0 | 108-16 | 2 |
| 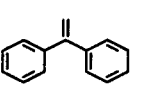 | 21 | 95.5 | 98-106 | 2 |
| 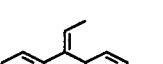 | 22 | 90.2 | 104-8 | 2 |
| 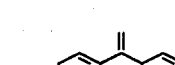 | 23 | 95.8 | 120-4 | 2 |
| 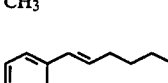 | 24 | 81.8 | 75 | 2 |
| 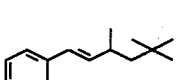 | 25 | 60.3 | 77 | 2 |
| 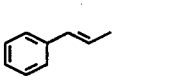 | 26 | — | 117-19 | — |
| 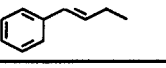 | 27 | — | 84 | 22 |

TABLE 4

Synthesis of 1,1-diphenyl-1-propenes, starting from propiophenone

| Structural formula | Ser. | Yield/% | Boiling range t/°C. | p/mbar |
|---|---|---|---|---|
| 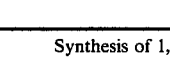 | 28 | 90.0 | 100-6 | 2 |
| 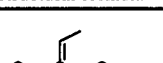 | 29 | — | 138 | 2 |
|  | 30 | — | 105 | 2 |
| 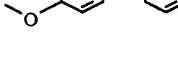 | 31 | 85.3 | 107 | 2 |
| 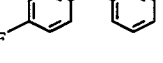 | 32 | — | 97-8 | 2 |

TABLE 5
Synthesis of 1,1-diphenylethylenes

| Structural formula | Ser. | Yield/% | Boiling range t/°C | p/mbar |
|---|---|---|---|---|
| (4-Cl-C6H4)(4-F-C6H4)C=CH2 | 33 | 92.8 | 106–8 | 2 |
| (4-Cl-C6H4)(C6H5)C=CH2 | 34 | 95.7 | 118–24 | 1 |
| (4-Cl-C6H4)(4-CH3-C6H4)C=CH2 | 35 | 88.6 | 128–32 | 1 |

TABLE 6
Synthesis of 1-aryl-1-alkenes via 1-aryl-1-alkanols obtained by the Guebet reaction

| Structural formula | Ser. | Yield/% | Boiling range t/°C | p/mbar |
|---|---|---|---|---|
|  | 36 | 90.0 | 115–18 | 2 |
|  | 37 | 88.0 | 111–12 | 2 |
|  | 38 | — | 128–30 | 4 |
|  | 39 | — | 146–7 | 2 |
|  | 40 | — | 104 | 2 |
|  | 41 | — | 123–4 | — |
|  | 42 | — | 125 | 2 |
|  | 43 | — | 167–8 | 18 |
|  | 44 | 90.4 | 146–8 | 80 |
|  | 45 | 88.7 | (m.p. 99–101) | |
|  | 47 | — | 78–9 | 4 |
|  | 48 | 92 | 124 | 2 |

(concluded overleaf)

We claim:

1. A process for the preparation of a 1-aryl-1-alkene, the process comprising dehydrating a 1-aryl-1-alkanol in the presence of a substance promoting elimination of water wherein said substance is a triester of phosphorous acid of the general formula (III)

$$R^4O—P(OR^5)—OR^6 \qquad (III)$$

wherein $R^4$, $R^5$, and $R^6$ are identical or different aryl, alkyl of from 1 to 20 carbon atoms, arylalkyl of from 7 to 20 carbon atoms, or cycloalkyl of from 3 to 8 carbon atoms, provided that at least one of $R^4$, $R^5$ and $R^6$ is aryl.

2. The process of claim 1 wherein the substance promoting elimination of water is a triaryl phosphite.

3. The process of claim 1 wherein the substance promoting elimination of water is triphenyl phosphite or tritolyl phosphite.

4. The process of claim 1 wherein the water formed by the reaction is removed with the aid of an entrainer.

5. The process of claim 1 wherein the 1-aryl-1-alkene is isolated by fractional distillation of the reaction mixture after elimination of water is completed, without the performance of any other purifying operation.